United States Patent [19]
Pongratz et al.

[11] Patent Number: 5,175,756
[45] Date of Patent: Dec. 29, 1992

[54] DEVICE FOR DETECTING NITROGENOUS, PHOSPHORIC, CHLORIC AND OXYGENOUS SUBSTANCES

[75] Inventors: Hans-Wolfgang Pongratz, Taufkirchen; Ingbert Bastian, Ottobrunn; Nikolaus Moritz, Taufkirchen; Werner Triftshäuser, Ottobrunn; Gottfried Kögel, München; Peter Sperr, Kirchheim, all of Fed. Rep. of Germany

[73] Assignee: Messerschmitt-Bölkow-Blohm GmbH, Fed. Rep. of Germany

[21] Appl. No.: 792,177

[22] Filed: Nov. 14, 1991

[30] Foreign Application Priority Data

Nov. 16, 1990 [DE] Fed. Rep. of Germany ....... 4036605

[51] Int. Cl.⁵ .................................... G01N 23/201
[52] U.S. Cl. ........................................ 378/88; 378/57; 378/62
[58] Field of Search .................. 378/57, 51, 46, 50, 378/45, 53, 62, 63, 86, 88, 87, 90

[56] References Cited

U.S. PATENT DOCUMENTS 4,864,142  9/1989  Gomberg .................. 378/57
4,941,162  7/1990  Vartsky et al. .......... 378/57

FOREIGN PATENT DOCUMENTS 0358237  3/1990  European Pat. Off. .

*Primary Examiner*—David P. Porta
*Attorney, Agent, or Firm*—Evenson, Wands, Edwards, Lenahan & McKeown

[57] ABSTRACT

A device for detecting nitrogenous, phosphoric, chloric and/or oxygenous substances inside an object, particularly of explosives or addictive substances in pieces of luggage. A nuclear activating device stimulates the emission of positron radiation from nitrogen, phosphorous, chlorine and/or oxygen, and an activity measuring device records positron-electron annihilation radiation.

17 Claims, 2 Drawing Sheets

DEVICE FOR DETECTING NITROGENOUS, PHOSPHORIC, CHLORIC AND OXYGENOUS SUBSTANCES

BACKGROUND AND SUMMARY OF THE INVENTION

This invention relates to a device for detecting nitrogenous, phosphoric, chloric and/or oxygenous substances inside an object, particularly explosives or addictive substances in pieces of luggage. According to the invention, a nuclear activating device stimulates the emission of positron radiation from nitrogen, phosphorous, chlorine and/or oxygen, and an activity measuring device records positron-electron annihilation radiation.

A device of this generic type is disclosed in European Patent Document EP 0 358 237 A1, in which pieces of luggage to be examined are guided on a conveyor belt through a radiation chamber and there are exposed to X-ray radiation (gamma radiation) of between 10.6 and 13.0 MeV. If nitrogenous substances are contained in the piece of luggage, indicating the presence of explosives, the X-ray radiation converts the $^{14}N$-atoms, into radioactive $^{13}N$-atoms, which emit positron radiation. When emitted positrons impinge on electrons, a known annihilation radiation of 0.511 MeV results. After being subjected to this type of radiation, the pieces of luggage are then transported to scintillation counters to detect the presence of any such released annihilation radiation. On the basis of the signals of the scintillation counters, conclusions are then drawn by means of a computer concerning the nitrogen concentration in the piece of luggage. However, the known arrangement furnishes no information on the spatial distribution of the nitrogenous substances in the piece of luggage, and can therefore supply only very rough information on the presence of explosives.

A more exact spatial resolution concerning the distribution of nitrogenous substances is possible by means of the device disclosed in European Patent Document EP 0 218 240 A2. However, this device is based on the activating process $^{14}N$ (gamma, 2n) $^{12}N$, for which X-ray radiation of at least 30.64 MeV is required. For this reason, the X-ray unit generates a bremsstrahlung of 35 to 40 MeV which, in a narrow beam, is used to scan the piece of luggage passing through on the conveyor belt. The resulting annihilation radiation is then recorded by means of two opposite detector lines on the basis of a coincidence measurement, and conclusions can be drawn from the geometrical relationships between the exciting X-ray beam and the detectors recording two isochronous 0.511 MeV photons concerning the location of a nitrogenous substance and the concentration of the nitrogenous substance present at that location in the piece of luggage.

It is an object of the present invention to provide a device suitable for detecting nitrogenous substances inside a piece of luggage as well as phosphoric, chloric and oxygenous substances, which permits a more exact spatial resolution of these substances than previously possible, and requires an activation energy that is as low as possible.

This object is achieved by the detection device constructed according to the invention, which is based on the generation of $^{13}N$-atoms from nitrogenous substances by subjecting them to X-ray radiation (bremsstrahlung) or gamma radiation with energies of from 10 MeV up to a maximum of 14 MeV. By means of a known coincidence measuring device, a first rough activity density distribution can then be derived for the examined piece of luggage. The piece of luggage is X-rayed by means of a separate X-ray unit which may be connected in front of or behind the activity measuring device, and a three-dimensional absorption density distribution is calculated from the projections of the absorption at at least two different X-ray energies. From the relationship between two absorption values of the same point of the piece of luggage which are measured at different X-ray beam energies, at least approximate conclusions can be drawn concerning the atomic number of the substance situated there. (Generally, it is sufficient to be able to differentiate between a few atomic number ranges in order to be able to detect the presence of metals which have a high absorption, but which are not part of the substances to be detected.) By means of the atomic number and the absorption density distribution, a nuclear density distribution can then be calculated, and the first activity density distribution can be corrected such that the reconstruction of a more exact three-dimensional activity density distribution inside the piece of luggage becomes possible.

By means of such a precise activity density distribution, when the activation energies are known, conclusions can be drawn more reliably than previously concerning the presence of explosives and addictive substances. In particular, when there is a first suspicion, a piece of luggage can be subjected to a second examination at the suspicious points during which, primarily through excitation by means of an energy of between 15 and 18 MeV, the presence of oxygenous substances and of the concentrations of these substances that are typical for explosives, can be determined.

Furthermore, to improve the false-alarm rate, an X-ray tomograph in addition to the first X-ray unit, can be provided for the exact measuring of the atomic number and absorption density distribution. In this manner, only those pieces of luggage are examined which were classified as being suspicious on the basis of a first measurement. As a result, the average examining speed is reduced only slightly since the more extensive examination by means of the X-ray tomograph is carried out only at a few pieces of luggage which in the preliminary examination had been classified as suspicious.

Other objects, advantages and novel features of the present invention will become apparent from the following detailed description of the invention when considered in conjunction with the accompanying drawings.

DETAILED DESCRIPTION OF THE DRAWINGS

Figure 1:
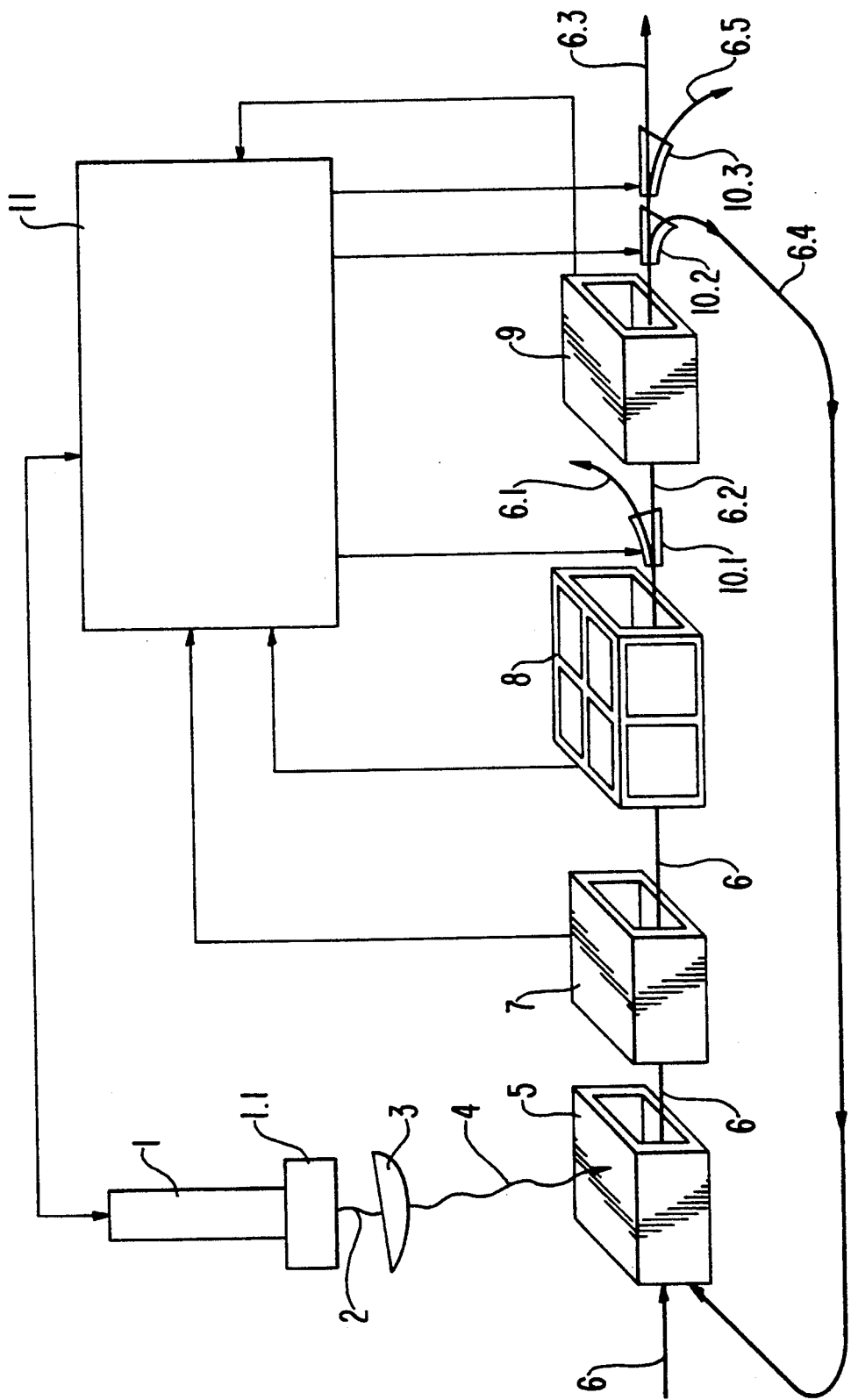
FIG. 1 is a of a facility for examining pieces of luggage for the presence of explosives or addictive substances.

The facility illustrated in FIG. 1 has an electron accelerator 1 of variable energy which is followed by a beam deflector 1.1. The generated electron beam 2 impinges on a heavy metal target, and thus creates a bremsstrahlung source 3, so that the bremsstrahlung 4 (gamma radiation) arrives in a tunnel-shaped radiation chamber 5 through which the conveyor belt 6 travels. Behind the radiation chamber 5, a tunnel-shaped X-ray unit 7 is arranged through which the conveyor belt also travels, and which is followed by a tunnel-shaped activity measuring device 8, such as a so-called Anger camera. The conveying path is then divided into two paths 6.1 and 6.2, conveying path 6.2 travelling through an also tunnel-shaped 3D X-ray tomograph 9. Then the conveying path 6.2 divides twice successively. On path 6.3, the pieces of luggage which, although they are initially identified as suspicious, are released after a final examination, reach the baggage reclaim section; on path 6.4, suspicious pieces of luggage which are not so released are conveyed back to the start of the facility for the purpose of a reexamination; and on path 6.5 the pieces of luggage which are finally classified as suspicious are conveyed further. The rerouting of the pieces of luggage onto paths 6.1 to 6.5 takes place by means of switches or sliders 10.1, 10.2 and 10.3 which are controlled by a central computer 11.

The electron accelerator 1 is controlled by the central computer 11 such that, in a first radiation cycle, the bremsstrahlung 4 has an energy range of from at least 10 to 14 MeV. The upper limit of 14 Mev is just below the threshold energy for the excitation of oxygen to a positron-radiating isotope, but is sufficient to excite substances like nitrogen, chlorine and phosphorus to form positron radiation emitters. The irradiation of a piece of luggage in this case takes place by line-by-line scanning of the electron beam (and thus of the generated bremsstrahlung 4), perpendicularly with respect to the conveying direction of the piece of luggage, so that it is subjected to radiation successively layer by layer.

The half-life of activated nitrogen atoms ($^{13}N$) is approximately 10 minutes, which is sufficiently long to permit X-ray examination of the luggage to determine a rough atomic number and absorption density distribution in the piece of luggage, prior to examination in the Anger camera 8. For this purpose, the piece of luggage is X-rayed by two or three X-ray sources, as described below, in order to establish an approximately three-dimensional absorption density reconstruction of the piece of luggage. Each of the X-ray sources may be an X-ray tube which emits a fan-shaped beam in a manner known to the prior art. In this case, the energy spectrum of each tube should have a range which extends from 10 keV to 140 keV. After passing through the luggage, the X-ray beam is detected by a linear array of detectors which, by means of suitable shielding, detect radiation in two energy bands, specifically $E_1$ less than 70 keV and $E_2$ from 90 to 140 keV.

Figure 2:
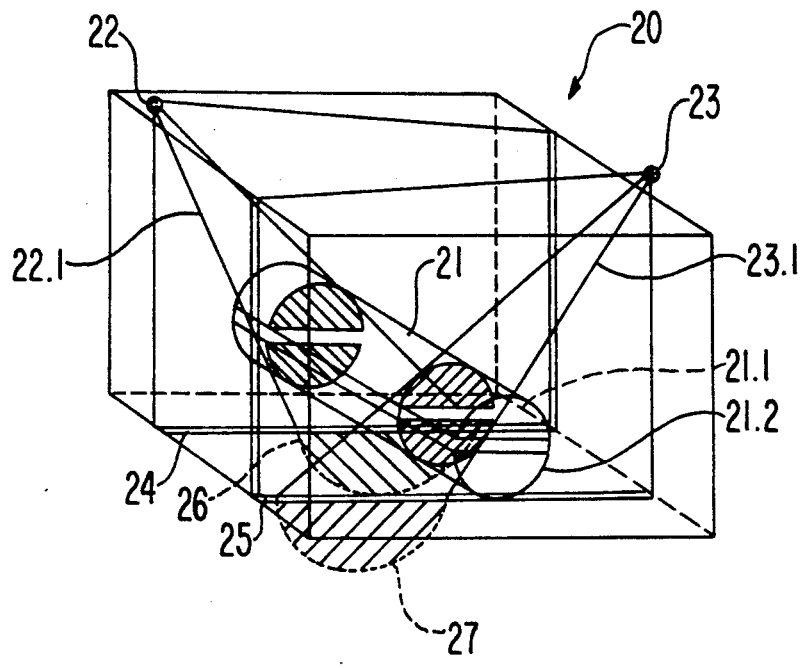
FIG. 2 is a view of an X-ray unit with two projections for the determination of the nuclear density distribution.

FIG. 2 illustrates the examination of a piece of luggage 21 inside an X-ray unit from two directions. The conveying shaft has a rectangular cross-section through which the luggage travels. Two X-ray sources 22 and 23 which emit a fan-shaped X-ray beam 22.1 and 23.1 are arranged on the upper edges of the shaft, offset with respect to the travelling direction. Each of the beams 22.1 and 23.1 impinges on an opposite L-shaped detector line 24 or 25 which measures the absorption of the X-ray radiation by the piece of luggage 21. That is, as a function of the contours of the piece of luggage on the detector lines 24 and 25, projections 26 and 27 are created which are assigned to the instantaneous site of the piece of luggage and are used to reconstruct the absorption density distribution.

As easily recognizable in FIG. 2, two projections are not sufficient for a clear reconstruction of the absorption density distribution. Two objects (21.1 and 21.2) which are situated behind one another in the X-ray beam inside a piece of luggage cannot be separated from one another by means of the projections.

Figure 3:
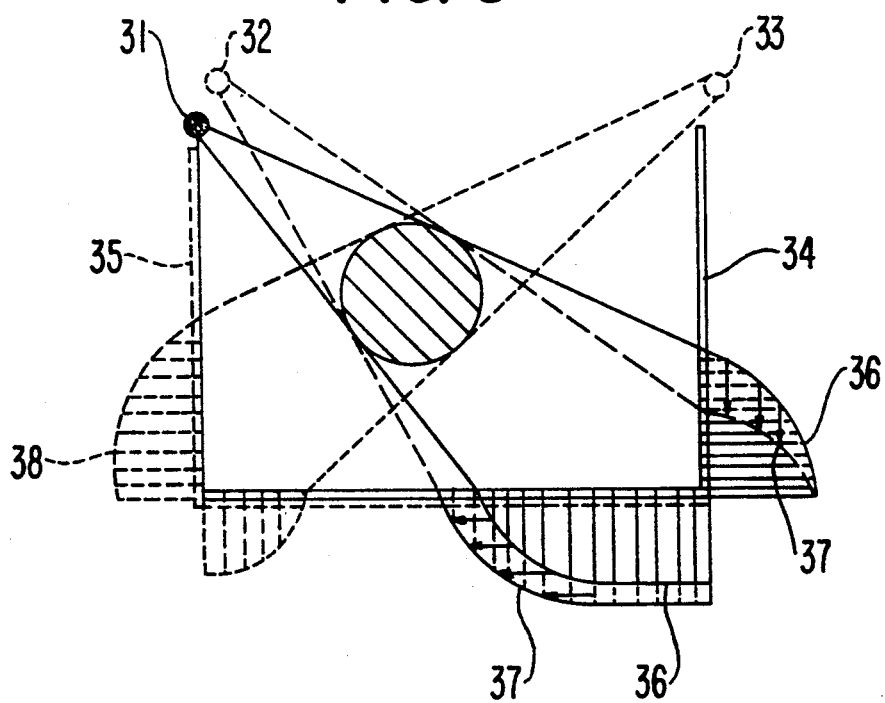
FIG. 3 is a view of an X-ray unit with additional projections for the determination of the nuclear density distribution with a higher local resolution.

In order to deal with this possibility, therefore, in a preferred embodiment of the invention, two X-ray sources 31 and 32 are situated on an edge of the conveying shaft relatively close to one another (FIG. 3) so that a stereoscopic image pair can be derived from a comparison of the absorption signals from the respective assigned L-shaped detector lines 34 and 35. (The stereo effect is indicated by arrows between the absorption signals 36 and 37.) As a result, the distance of absorbing objects inside the piece of luggage can be determined by known stereo evaluation techniques. As a result of the absorption signal 38 arising from the opposite X-ray source 33, which is therefore created at an angle of almost 90° with respect to the other projections, the contours of the objects recognized in the stereoscopic image can be better displayed. Furthermore, the depth position of an object can be calculated from the stereoscopic image, which can be correlated with the third projection, and the formation of spurious objects from erroneous or ambiguous correlations can thus be avoided. As a result, an approximate reconstruction of the three-dimensional density distribution from the X-ray images from only three projections becomes possible; whereas, for an exact reconstruction approximately as many projections would be required as indicated by the image resolution of the detector lines in pixels along the edge of the image which, however, would not be possible for an examination of pieces of luggage with a realistic time consumption.

Furthermore, the relationship of the examined length (in the direction of movement of the piece of luggage) to the width and height (transversely to the direction of movement) is selected such that a point on the longitudinal axis of the detector unit approximately in the center thereof is surrounded by detector elements in a large solid angle area. If possible, the solid angle in this case should be larger than 60% of $4\pi$. As a result, the method described for example, in IIIE-Transactions Medical Imaging, Vol. MI-2/1983, Pages 16 to 18, may be used.

After a piece of luggage has travelled through the X-ray unit 7 for the reconstruction of the absorption density distribution, it arrives in a so-called Anger camera which is essentially a position-resolving detector system for the annihilation radiation occurring from positron annihilation. On the basis of coincidence measurements, a list of coincidence events is established which is converted in the computer 11 into a first activity density distribution of the piece of luggage. In this case, the "PENNPET" instrument of the firm UGM Medical Systems, Phil., USA, is suitable for use as the Anger camera.

So that the Anger camera detectors can also measure objects which move through the measurement chamber of the Anger camera at a constant speed, it is necessary to determine the respective position of the object in the longitudinal direction and to immediately correct the measured impinging points of opposite directed photons (gamma rays) resulting from annihilation events onto the detector elements, by adding the respective offset in the longitudinal direction due to such longitudinal movement. Thus, all event lines connecting the measured impinging points can be corrected to the same reference point with respect to the measured object and may therefore be processed as if they were to originate from a measurement on a stationary object. As a result, objects can in principle be measured in the Anger camera which have an arbitrary length, and their throughput through the facility can therefore be increased.

By correlating a derived mass density distribution which was determined from the absorption density distributions at two different X-ray beam energies as described above, with the first approximation of the activity density distribution determined from the values of the Anger camera, a better second approximation of the three-dimensional activity density distribution of the object can be calculated.

Pieces of luggage, which do not exhibit a given activity density, are guided to the luggage reclaiming section by means of a switch 10.1 controlled by the computer 11 (FIG. 1). When a specific amount of activity is exhibited, the piece of luggage will travel into an X-ray tomograph 9 in which a precisely three-dimensional absorption density distribution, particularly of the areas of increased activity density, is carried out. If this measurement does not result in an absorption density distribution that is suspicious with respect to explosives, the piece of luggage is released by way of switches 10.2 and 10.3, which are also computer-controlled. However, if the areas of increased activity are also situated within an absorption density area which is relevant with respect to explosives, the piece of luggage by way of switch 10.2 will travel on the conveying path 6.4 back into the radiation chamber 5 where it is subjected to another radiation at a second (higher) energy level of between 15 and 18 MeV, a second activity density distribution is determined from the higher radiation energy level, and the values for the activity density distribution are subtracted from those of the second activity density distribution. Radiation (bremsstrahlung) in this energy range (threshold energy at 15.7 megaelectron volt) excites the nuclear reaction $^{16}O$ ($\gamma$, n) $^{15}O$, but is still below the threshold of 18.7 MeV for the activation of carbon corresponding to the nuclear reaction $^{12}C$ ($\gamma$, n) $^{11}C$.

Then, after approximately 30 seconds when the activity of the also excited aluminum has decayed, another measurement takes place by means of the Anger camera in order to determine whether there is, in the suspicious space area of the piece of luggage, in addition to nitrogen, also a sufficient amount of oxygen in order to indicate an explosive in this combination. If the ratio of nitrogen to oxygen is in a range that is critical for explosives and if the amount is sufficient, another stronger clue exists for the presence of an explosive, and the switch 10.3 at the end of the conveyor belt is then switched for the selection of the piece of luggage on the conveying path 6.5.

In the same manner as nitrogen, the elements chlorine, phosphorus and, if present in explosives, fluorine, can also be detected which, in the case of x-rays (bremsstrahlung) $\gamma$-radiation, are also excited to form positron-emitting isotopes, specifically according to the following nuclear reactions with the indicated threshold energies:

$^{35}Cl$ ($\gamma$, n) $^{34}Cl$ at (12.8 MeV), $^{31}P$ ($\gamma$, n) $^{30}P$ at (12.3 MeV)

and $^{19}F$ ($\gamma$, n) $^{18}F$ at (10.4 MeV).

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. Apparatus for detecting nitrogenous, phosphoric, chloric and oxygenous substances contained in an object, said apparatus comprising:

nuclear activating means (1, 1.1, 3, 5) for causing at least one of said nitrogenous, phosphoric, chloric or oxygenous substances to emit positron radiation by exposing said object to radiation at a first energy level;

activity measuring means (8) for recording positron-electron annihilation radiation generated within said object;

means for determining a first activity density distribution within said object on the basis of coincidence measurements made by said activity measuring means within said object at said first energy level;

X-ray means (7) for detecting projections created by absorption of radiation within said object, said X-ray means having means for detecting at least two different energy levels of X-rays;

means (11) for determining a three dimensional absorption density distribution, comprising at least two absorption values for each of a multiplicity of points within said object, based on said projections detected by said X-ray means at each of said at least two different energy levels of X-rays;

means (11) for comparing said at least two absorption values at respective points within said object and for discriminating at least two atomic number ranges for substances at points within said object to determine an atomic number and absorption density distribution within said object; and means (11) for correlating said activity density distribution and said atomic number and absorption density distribution and for constructing a corrected three dimensional activity density distribution within said object.

2. Apparatus according to claim 1, wherein said nitrogenous, phosphoric, chloric and oxygenous substances are at least one of: explosives or addictive substances.

3. Apparatus according to claim 1, wherein a conveyor belt (6) conveys said object through the activity measuring means (8) and the X-ray means (7), points within said object being measured in both of said X-ray and activity measuring means relative to an identical spatial reference.

4. Apparatus according to claim 2, wherein said X-ray means (7) is situated immediately before or after said activity measuring means (8) relative to a direction of movement of said conveyor belt (6).

5. Apparatus according to claim 1, wherein the nuclear-activating means (1, 3, 5) generates gamma radiation (4) with at least two different energy levels.

6. Apparatus according to claim 3, wherein the nuclear activating means (1, 3, 5) generates gamma radiation (4) with at least two different energy levels.

7. Apparatus according to claim 5, wherein the nuclear activating device (1, 3, 5) generates gamma radiation (4) with an energy level which is one of: between 10 and 14 MeV, and between 15 and 18 MeV.

8. Apparatus according to claim 5, wherein:
said conveyor belt includes means for causing said object to be conveyed through said nuclear activating means a second time;
said nuclear activating means includes means for exposing said object to radiation at a second energy level which is greater than said first energy level; and
said means for determining a first activity density distribution includes means for determining a second activity density distribution within said object at said second energy level, and for subtracting values contained in said first activity density distribution from corresponding values contained in said second density distribution.

9. Apparatus according to claim 6, wherein:
said conveyor belt includes means for causing said object to be conveyed through said nuclear activating means a second time;
said nuclear activating means includes means for exposing said object to radiation at a second energy level which is greater than said first energy level; and
said means for determining a first activity density distribution includes means for determining a second activity density distribution within said object at said second energy level, and for subtracting values contained in said first activity density distribution from corresponding values contained in said second density distribution.

10. Apparatus according to claim 7, wherein:
said conveyor belt includes means for causing said object to be conveyed through said nuclear activating means a second time;
said nuclear activating means includes means for exposing said object to radiation at a second energy level which is greater than said first energy level; and
said means for determining a first activity density distribution includes means for determining a second activity density distribution within said object at said second energy level, and for subtracting values contained in said first activity density distribution from corresponding values contained in said second density distribution.

11. Apparatus according to claim 8, wherein the second exposure of the object to radiation is limited to ranges of increased activity density or absorption density.

12. Apparatus according to claim 10, wherein the second exposure of the object to radiation is limited to ranges of increased activity density or absorption density.

13. A device according to claim 1, wherein the nuclear activating means (1, 3, 5) has a predetermined pattern in the emitted radiation dosage.

14. A device according to claim 1, wherein the X-ray unit (7) comprises means for generating projections of the absorption from at least three different directions.

15. A device according to claim 14, wherein two of the three directions differ only slightly, whereby a stereoscopic evaluation of the measured absorption values is possible.

16. A device according to claim 1, which further comprises an X-ray tomograph (9) for the exact measurement of the atomic number and absorption density distribution inside an object which is preselected by means of the nuclear activity measuring device (8) and the first X-ray unit (7).

17. A method for detecting nitrogenous, phosphoric, chloric and/or oxygenous substances inside an object, comprising the steps of:
activating at least one of nitrogen, phosphorous, chlorine atoms and oxygen atoms by means of gamma radiation, to cause said atoms to emit positron radiation;
measuring positron-electron annihilation radiation generated inside the largest part of a solid angle surrounding the object;
examining the object by means of an X-ray radiation with at least two different energy levels;
determining an atomic number and absorption density distribution from measured absorption values of several projections of the object; and
calculating a three-dimensional activity density distribution from the measured values according to said measuring step, taking into account the detailed atomic number and absorption density distribution.

* * * * *